(12) United States Patent
Menmuir et al.

(10) Patent No.: US 12,156,684 B2
(45) Date of Patent: Dec. 3, 2024

(54) SYSTEMS AND METHODS FOR PROMOTING SACROILIAC JOINT FUSION

(71) Applicant: NuVasive, Inc., San Diego, CA (US)

(72) Inventors: Brett Menmuir, Reno, NV (US); Morton Albert, Carlsbad, CA (US); Dan Zatta, San Diego, CA (US)

(73) Assignee: NuVasive, Inc., San Diego, CA (US)

(*) Notice: Subject to any disclaimer, the term of this patent is extended or adjusted under 35 U.S.C. 154(b) by 381 days.

(21) Appl. No.: 17/647,980

(22) Filed: Jan. 14, 2022

(65) Prior Publication Data

US 2022/0133375 A1    May 5, 2022

Related U.S. Application Data

(60) Division of application No. 16/184,258, filed on Nov. 8, 2018, now Pat. No. 11,253,302, which is a continuation of application No. 13/830,028, filed on Mar. 14, 2013, now Pat. No. 10,179,014.

(60) Provisional application No. 61/716,422, filed on Oct. 19, 2012, provisional application No. 61/654,320, filed on Jun. 1, 2012.

(51) Int. Cl.
*A61B 17/86*    (2006.01)
*A61B 17/70*    (2006.01)
*A61B 17/88*    (2006.01)

(52) U.S. Cl.
CPC ...... *A61B 17/8605* (2013.01); *A61B 17/7055* (2013.01); *A61B 17/7082* (2013.01); *A61B 17/8615* (2013.01); *A61B 17/864* (2013.01); *A61B 17/869* (2013.01); *A61B 17/8816* (2013.01); *A61B 17/8888* (2013.01); *A61B 17/8822* (2013.01)

(58) Field of Classification Search
CPC ............................................ A61B 17/86–8695
See application file for complete search history.

(56) References Cited

U.S. PATENT DOCUMENTS

| | | |
|---|---|---|
| 4,292,964 A | 10/1981 | Ulrich |
| 4,569,338 A | 2/1986 | Edwards |
| 4,612,918 A | 9/1986 | Slocum |
| 5,034,011 A | 7/1991 | Howland |
| 5,133,717 A | 7/1992 | Chopin |
| 5,334,205 A | 8/1994 | Cain |
| 5,489,307 A * | 2/1996 | Kuslich .................. A61F 2/446 606/279 |
| 5,490,851 A | 2/1996 | Nenov et al. |
| 5,593,407 A | 1/1997 | Reis |
| 5,643,264 A | 7/1997 | Sherman et al. |

(Continued)

FOREIGN PATENT DOCUMENTS

| | | |
|---|---|---|
| CN | 2265765 | 10/1997 |
| CN | 2265768 | 10/1997 |

(Continued)

*Primary Examiner* — Zade Coley (57) ABSTRACT

Embodiments are directed to fusion implants, insertion instruments, and methods of using the same for implanting one or more fusion implants across a sacroiliac joint and into an ilium and sacrum for fusing the sacroiliac joint. In some cases, fusion-promoting material may be inserted in the fusion implant for further promoting fusion across the sacroiliac joint. In some cases, neurophysiologic monitoring may be performed as the fusion implants are placed across the sacroiliac joint.

16 Claims, 8 Drawing Sheets

(56) References Cited

U.S. PATENT DOCUMENTS

| | | | |
|---|---|---|---|
| 5,683,217 A * | 11/1997 | Walther | F16B 35/06 411/399 |
| 5,713,904 A | 2/1998 | Errico et al. | |
| 5,928,239 A | 7/1999 | Mirza | |
| 5,941,911 A * | 8/1999 | Buechel | A61F 2/38 606/101 |
| 6,033,405 A * | 3/2000 | Winslow | A61F 2/4611 606/86 R |
| 6,053,916 A * | 4/2000 | Moore | A61F 2/30988 606/86 R |
| RE36,741 E * | 6/2000 | Walther | F16B 35/065 411/399 |
| 6,146,380 A | 11/2000 | Racz et al. | |
| 6,214,004 B1 | 4/2001 | Coker | |
| 6,565,572 B2 * | 5/2003 | Chappius | A61B 17/7092 600/300 |
| 6,635,059 B2 | 10/2003 | Randall et al. | |
| 6,648,903 B1 | 11/2003 | Pierson, III | |
| 7,293,947 B2 * | 11/2007 | Craven | F16B 35/048 411/399 |
| 7,338,493 B1 * | 3/2008 | Vandewalle | A61B 17/7098 606/86 A |
| 7,386,350 B2 | 6/2008 | Vilims | |
| 7,575,572 B2 * | 8/2009 | Sweeney | A61B 17/8685 604/264 |
| 7,608,097 B2 * | 10/2009 | Kyle | A61B 17/864 606/93 |
| 7,625,395 B2 | 12/2009 | Muckter | |
| 7,648,509 B2 | 1/2010 | Stark | |
| 7,670,383 B1 | 3/2010 | Brown et al. | |
| 7,789,895 B2 | 9/2010 | Heinz | |
| 7,794,484 B2 * | 9/2010 | Stone | A61B 17/0401 606/92 |
| 7,799,021 B2 | 9/2010 | Leung et al. | |
| 7,819,869 B2 | 10/2010 | Godara et al. | |
| 7,850,719 B2 | 12/2010 | Gournay et al. | |
| 7,922,765 B2 | 4/2011 | Reiley | |
| 7,938,834 B2 | 5/2011 | Roush | |
| 7,967,847 B2 | 6/2011 | Barker, Jr. et al. | |
| 8,052,726 B2 | 11/2011 | Nayet et al. | |
| 8,066,702 B2 | 11/2011 | Rittman, III et al. | |
| 8,858,145 B2 * | 10/2014 | Su | F16B 35/065 411/399 |
| 2002/0198527 A1 | 12/2002 | Muckter | |
| 2004/0138662 A1 * | 7/2004 | Landry | A61B 17/861 606/279 |
| 2004/0193157 A1 | 9/2004 | Falahee | |
| 2004/0228901 A1 | 11/2004 | Trieu et al. | |
| 2005/0101961 A1 * | 5/2005 | Huebner | A61B 17/8605 606/305 |
| 2005/0101964 A1 | 5/2005 | Lin et al. | |
| 2005/0154391 A1 | 7/2005 | Doherty et al. | |
| 2005/0267482 A1 | 12/2005 | Hyde | |
| 2006/0054171 A1 | 3/2006 | Dall | |
| 2006/0200121 A1 | 9/2006 | Mowery | |
| 2007/0027449 A1 | 2/2007 | Godara et al. | |
| 2007/0027543 A1 | 2/2007 | Gimble et al. | |
| 2007/0156136 A1 | 7/2007 | Godara et al. | |
| 2007/0265621 A1 | 11/2007 | Matthis et al. | |
| 2007/0270879 A1 | 11/2007 | Isaza et al. | |
| 2007/0299445 A1 | 12/2007 | Shadduck et al. | |
| 2007/0299482 A1 | 12/2007 | Littlewood et al. | |
| 2008/0009927 A1 | 1/2008 | Vilims | |
| 2008/0021454 A1 | 1/2008 | Chao et al. | |
| 2008/0021455 A1 | 1/2008 | Chao et al. | |
| 2008/0021456 A1 | 1/2008 | Gupta et al. | |
| 2008/0065069 A1 | 3/2008 | Betz et al. | |
| 2008/0140082 A1 | 6/2008 | Erdem et al. | |
| 2008/0234665 A1 | 9/2008 | Godara et al. | |
| 2008/0305145 A1 | 12/2008 | Shelby et al. | |
| 2009/0024174 A1 | 1/2009 | Stark | |
| 2009/0099610 A1 | 4/2009 | Johnson et al. | |
| 2009/0162376 A1 | 6/2009 | Brown et al. | |
| 2009/0171391 A1 * | 7/2009 | Hutton | A61B 17/8861 606/301 |
| 2009/0181892 A1 | 7/2009 | Thorne et al. | |
| 2009/0216238 A1 | 8/2009 | Stark | |
| 2009/0259261 A1 | 10/2009 | Reiley | |
| 2010/0042149 A1 | 2/2010 | Chao et al. | |
| 2010/0094290 A1 | 4/2010 | Vaidya | |
| 2010/0179562 A1 | 7/2010 | Linker et al. | |
| 2010/0191234 A1 | 7/2010 | Haufe | |
| 2010/0256688 A1 * | 10/2010 | Giersch | A61B 17/864 606/301 |
| 2010/0268228 A1 | 10/2010 | Petersen | |
| 2011/0009869 A1 | 1/2011 | Marino et al. | |
| 2011/0034957 A1 | 2/2011 | Biedermann | |
| 2011/0087289 A1 | 4/2011 | Pham et al. | |
| 2011/0098753 A1 | 4/2011 | Giger et al. | |
| 2011/0098816 A1 | 4/2011 | Jacob et al. | |
| 2011/0098817 A1 | 4/2011 | Eckhardt et al. | |
| 2011/0166575 A1 | 7/2011 | Assell et al. | |
| 2011/0166658 A1 | 7/2011 | Garber et al. | |
| 2011/0184478 A1 | 7/2011 | Reiley | |
| 2011/0184518 A1 | 7/2011 | Trieu | |
| 2011/0184519 A1 | 7/2011 | Trieu | |
| 2011/0184520 A1 | 7/2011 | Trieu | |
| 2011/0230966 A1 | 9/2011 | Trieu | |
| 2011/0238181 A1 | 9/2011 | Trieu | |
| 2011/0264275 A1 | 10/2011 | Donner | |
| 2011/0268820 A1 | 11/2011 | Stark | |
| 2011/0288598 A1 | 11/2011 | Moed et al. | |
| 2011/0295272 A1 | 12/2011 | Assell et al. | |
| 2012/0022535 A1 | 1/2012 | Mayer et al. | |
| 2012/0022595 A1 | 1/2012 | Pham et al. | |
| 2013/0018427 A1 * | 1/2013 | Pham | A61B 17/8695 606/301 |
| 2013/0144344 A1 * | 6/2013 | Giancola | A61B 17/742 606/304 |

FOREIGN PATENT DOCUMENTS

| | | |
|---|---|---|
| CN | 2298783 | 12/1998 |
| CN | 2551205 | 5/2003 |
| CN | 2655820 | 11/2004 |
| CN | 2657596 | 11/2004 |
| CN | 1644175 | 7/2005 |
| CN | 1666718 | 9/2005 |
| CN | 2762772 | 3/2006 |
| CN | 201073333 | 6/2008 |
| CN | 201139628 | 10/2008 |
| CN | 201211225 | 3/2009 |
| CN | 201275132 | 7/2009 |
| CN | 201275133 | 7/2009 |
| CN | 201275134 | 7/2009 |
| CN | 201586066 | 9/2010 |
| CN | 201602870 | 10/2010 |
| CN | 201612688 | 10/2010 |
| CN | 201631359 | 11/2010 |
| CN | 201734774 | 2/2011 |
| CN | 201899554 | 7/2011 |
| CN | 102274070 | 12/2011 |
| EP | 1600112 | 11/2005 |
| EP | 1961394 | 8/2008 |
| FR | 2870713 | 12/2005 |
| FR | 2894454 | 6/2007 |
| JP | 2003135476 | 5/2003 |
| KR | 20090058371 | 6/2009 |
| RU | 2157669 | 10/2000 |
| RU | 2199284 | 2/2003 |
| RU | 2248765 | 3/2005 |
| RU | 2004100759 | 7/2005 |
| RU | 2284164 | 9/2006 |
| RU | 2306895 | 9/2007 |
| RU | 2309696 | 11/2007 |
| RU | 2328998 | 7/2008 |
| RU | 2354318 | 5/2009 |
| RU | 2364359 | 8/2009 |
| RU | 2381759 | 2/2010 |
| RU | 2428136 | 9/2011 |
| SU | 1456123 | 2/1989 |

(56) References Cited

FOREIGN PATENT DOCUMENTS

| | | | |
|---|---|---|---|
| SU | 1621902 | 1/1991 | |
| TW | 201103492 | 2/2011 | |
| UA | 71828 | 12/2004 | |
| WO | WO199523559 | 12/2004 | |
| WO | WO200180738 | 12/2004 | |
| WO | WO2006127727 | 11/2006 | |
| WO | WO2007006158 | 1/2007 | |
| WO | WO2008088685 | 7/2008 | |
| WO | WO2008146982 | 12/2008 | |
| WO | WO2009029074 | 3/2009 | |
| WO | WO2010065015 | 6/2010 | |
| WO | WO2010104576 | 9/2010 | |
| WO | WO2010104577 | 9/2010 | |
| WO | WO2011158193 | 12/2011 | |
| WO | WO-2011158193 A1 * | 12/2011 | ......... A61B 17/7098 |
| WO | WO2012015976 | 2/2012 | |

\* cited by examiner

SYSTEMS AND METHODS FOR PROMOTING SACROILIAC JOINT FUSION

CROSS REFERENCES TO RELATED APPLICATIONS

The present application is a divisional application of U.S. patent application Ser. No. 16/184,258 filed Nov. 8, 2018 now U.S. Pat. No. 11,253,302, issued Feb. 22, 2022, which is a continuation of U.S. patent application Ser. No. 13/830,028 filed on Mar. 14, 2013, now U.S. Pat. No. 10,1790,148 issued Jan. 15, 2019; which claims the benefit of priority under 35 USC § 119(e) from U.S. Provisional Application Ser. No. 61/654,320 filed on Jun. 1, 2012 and entitled "Systems and Methods for Performing Neurophysiologic Monitoring During Sacroiliac Surgery," and U.S. Provisional Application Ser. No. 61/716,422 filed on Oct. 19, 2012 and entitled "Systems and Methods for Promoting Sacroiliac Joint Fusion," the entire contents of all of which are hereby incorporated by reference into this disclosure as if set forth fully herein. This application also incorporates by reference the entire contents of commonly owned U.S. Pat. No. 8,255,045, issued Aug. 28, 2012 entitled "Neurophysiology Monitoring System."

FIELD OF INVENTION

The present application relates generally to surgery and, more particularly, to fusion of the sacroiliac joint.

BACKGROUND

Every year, millions of Americans are diagnosed with lower back pain and, in up to 22% of cases, the causes of the pain originate from the sacroiliac joint. For cases of degenerative sacroiliitis, inflammatory sacroiliitis, iatrogenic instability of the sacroiliac joint, osteitis condesans ilii (OCI), and traumatic fracture dislocation of the pelvis, surgeons commonly employ stabilization and/or fusion at the sacroiliac joint; however, a growing body of research suggests that sacroiliac joint fusion may also be effective in treating lower back pain. The sacroiliac joints are diarthrodial synovial joints, connecting the sacrum to the ilium, that facilitate transmission of forces between the spine and the lower extremities; there is one sacroiliac joint on the left side of the sacrum and one sacroiliac joint on the right. The sacrum and the ilium are particularly coarsely textured with several ridges and depressions throughout both respective surfaces.

Additionally, the sacroiliac joint contains a very narrow joint space between the ilium and the sacrum. Despite its relatively small size, the biomechanics of the sacroiliac joint are complex, with movement occurring both in the transverse and the sagittal planes. Stability between the two surfaces is maintained by a combination of strong sacroiliac, sacrotuberous and sacrospinous ligaments, bony interdigitation, and several muscles that act directly upon the region. Due to the sacroiliac joint's anatomical location, examinations and research can often be difficult. However, with modern medical imaging systems such as computer tomography, magnetic resonance imaging, and fluoroscopic guidance, understanding and treating disorders at this joint are becoming increasingly effective.

SUMMARY

The present invention provides a sacroiliac fusion system and related methods for fixing a fusion implant across the sacroiliac joint as well as intraoperative neurophysiologic monitoring methods for monitoring the health and status of nerves near the fusion site during implant placement.

Some embodiments are directed to a system for fusing a sacroiliac joint. The sacroiliac fusion system may include a fusion implant having a main body dimensioned for placement across a sacroiliac joint, wherein the main body may have at least one fusion aperture. In addition, the fusion implant may have a distal end and a proximal end, with the proximal end including a coupling head for attaching to an insertion instrument. Furthermore, the sacroiliac fusion system may include an insertion device for implanting the fusion implant across a sacroiliac joint.

Some embodiments disclosed herein are directed to an insertion device for implanting a fusion implant across a sacroiliac joint. An embodiment of the insertion device may include an inner shaft having a proximal end and a distal end, with the distal end having at least one thread for engaging the fusion implant. In addition, the insertion device may include an outer shaft having a proximal end and a distal end, with the distal end having at least one counter-torque feature for engaging a counter-torque feature of the fusion implant. Furthermore, some insertion device embodiments may include a pusher having a proximal end and a distal end, with the distal end including a head for pushing fusion-promoting material into the fusion implant.

Some methods of implanting the fusion implant across a sacroiliac joint include at least the steps of securing a fusion implant to a distal end of an insertion instrument and inserting the fusion implant across the sacroiliac joint and into a sacrum and ilium. After insertion of the fusion implant across the sacroiliac joint, the step of releasing the insertion device from the fusion implant may be performed.

Some methods of performing neurophysiologic monitoring include monitoring the proximity, health and status of nerves near the fusion site as the implant is advanced from the skin, through the surgical corridor, and into its final position within the sacral iliac joint.

Certain embodiments are described further in the following description, examples, claims and drawings.

BRIEF DESCRIPTIONS OF THE DRAWINGS

Many advantages of the present invention will be apparent to those skilled in the art with a reading of this specification in conjunction with the attached drawings, wherein like reference numerals are applied to like elements and wherein.

The drawings illustrate embodiments of the invention and are not limiting. For clarity and ease of illustration, the drawings are not made to scale and, in some instances, various aspects may be shown exaggerated or enlarged to facilitate an understanding of particular embodiments.

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The sacroiliac fusion system and methods described herein boast a variety of inventive features and components that warrant patent protection, both individually and in combination.

Embodiments of the invention are directed generally to methods and devices for the treatment of one or more sacroiliac joints within the body of a patient. In particular, devices and methods described herein may be used for the fusion of a sacroiliac joint, as will be described in greater detail below.

Some embodiments of a sacroiliac fusion system are described herein in accordance with aspects of the present invention for fixing a fusion implant across the sacroiliac joint and into the sacrum and ilium. The sacroiliac fusion system may be comprised of at least one or more of a fusion implant and insertion device. After implantation across the sacroiliac joint, the fusion implant may secure the positioning of the sacrum relative to the ilium and promote the formation of a bony bridge therebetween. The fusion implant may be implanted through the ilium, across the sacroiliac joint, and into the sacrum. Additionally, the fusion implant may be inserted into the body of a patient using any number of approaches, including lateral, anterior, antero-lateral, and postero-lateral approaches. Some embodiments of the fusion implant may be comprised of non-bone compositions having radiolucent characteristics, including polymer compositions (e.g., poly-ether-ether-ketone (PEEK) and/or poly-ether-ketone-ketone (PEKK)) or any combination of PEEK and PEEK. In addition, other suitable materials may be used, including ceramics and metals, such as, by way of example, titanium.

In addition, fusion may be facilitated or augmented by introducing or positioning various fusion-promoting materials within and/or adjacent to the fusion implant. Such materials may be introduced before, during, or after the insertion of the fusion implant and may include, but are not limited to, autologous bone harvested from the patient, bone allograft, mesenchymal-stem-cell-based-products (e.g. Osteocel® Plus), bone xenograft, any number of non-bone implants (e.g. ceramic, metallic, polymer), bone morphogenetic protein, and bio-resorbable compositions including but not limited to any of a variety of poly (D, L-lactide-co-glycolide)-based polymers.

Some embodiments of the insertion devices described herein may include features that assist in the positioning and securing of the fusion implant across the sacroiliac joint, as well as assist in securing the fusion implant to the sacrum and ilium. Furthermore, some embodiments of the insertion device may include an instrument for assisting in the insertion and packing of fusion-promoting materials within the fusion implant, as will be described by way of example below.

FIGS. 1-4 illustrate an example embodiment of a fusion implant 10 which may include an elongated main body 12 extending from a coupling head 14. The fusion implant 10 may be cannulated with a through-hole 16 extending along a longitudinal axis $A_1$ of the fusion implant 10. The through-hole 16 may be used for guiding the fusion implant 10 over a positioning tool or insertion trajectory, such as a Steinmann pin or k-wire. Additionally, one or more fusion-promoting materials may be inserted in the through-hole 16 before, during or after implantation of the fusion implant 10 in order to assist in promoting fusion across the sacroiliac joint. In general, the fusion implant 10 may be any size and shape necessary to fix the positioning of the sacrum relative to the ilium and assist in fusing the sacroiliac joint. For example, the length of the fusion implant 10 may be, but is not limited to, between 10 mm and 100 mm. By way of further example, the diameter of at least the main body 12 may be, but is not limited to, between 5 mm and 15 mm.

Figure 1:
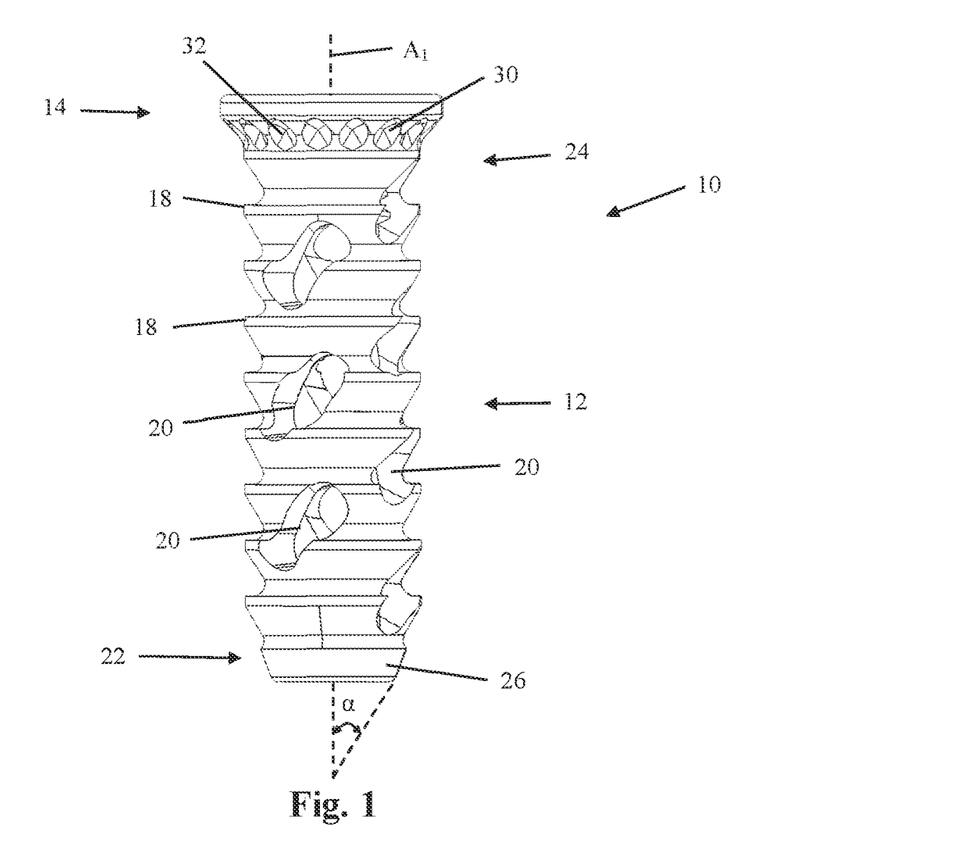
FIG. 1 illustrates a side view of an embodiment of a fusion implant of a sacroiliac fusion system for promoting fusion of a sacroiliac joint.
Figure 2:
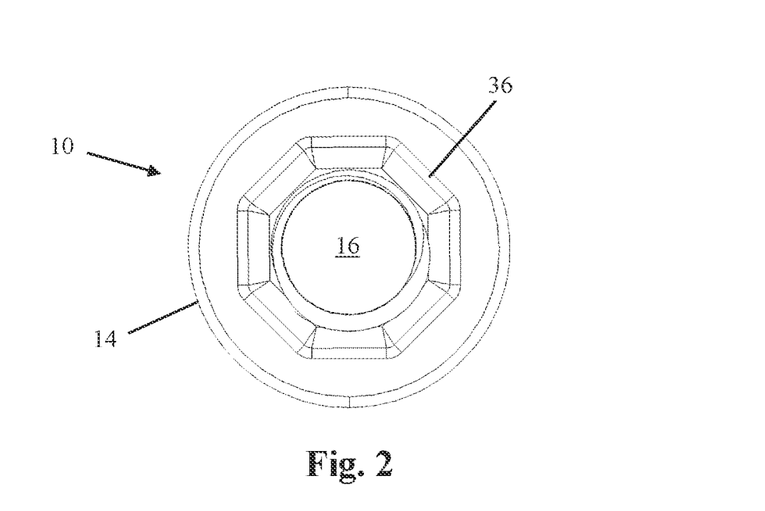
FIG. 2 illustrates a top view of the fusion implant of FIG. 1 showing the through-hole extending through the fusion device and which may be packed with a fusion-promoting material.

The fusion implant 10 may include one or more anti-migration features 18 along the exterior wall of the main body 12. The anti-migration features 18 may assist in preventing unwanted movement of the fusion implant 10 after implantation. For example, the anti-migration features 18 may include one or more angled ridges, as shown in FIG. 1. Additionally, the anti-migration features 18 may include one or more spikes, pyramidal features, and/or linear features extending from the outer surface of the main body 12. By way of further example, the anti-migration features 18 may include textured surfaces along the main body, or any combination thereof. Furthermore, the anti-migration features 18 may be angled or oriented such that they permit movement of the fusion implant 10 in the direction of insertion into a bone, such as the iliac and sacrum, but may resist movement in the opposing direction. This orientation of the anti-migration features 18 may allow at least the main body 12 of the fusion implant 10 to be inserted without the need for excessive force, while also assisting in the prevention of back-out or slippage in the opposing direction of insertion. In addition, some embodiments of the fusion implant 10 may include anti-migration features 18 that extend in a helical pattern around the exterior wall of the main body 12, and which may also assist in the insertion of the main body 12 during implantation.

The main body 12 of the fusion implant 10 may also include one or more fusion apertures 20 that extend through a part of the main body 12 and which may intersect with the through-hole 16. The fusion apertures 20 may allow bony bridges to form across the fusion implant 10, which may assist in further securing the fusion implant 10 and fusing the sacroiliac joint. In addition, a fusion-promoting material may be inserted within the fusion implant 10, such as in the through-hole 16, in order to further assist in the formation of bony bridges through at least the fusion apertures 20 and to fuse the sacroiliac joint. Furthermore, the fusion apertures 20 may be any size and shape necessary to allow the formation of bony bridges through the fusion apertures 20. For example, the fusion apertures may be any number of shapes including at least circular, rectangular, oval, triangular, or any combination thereof. In addition, for example, the fusion apertures may have a diameter between 1 mm and 10 mm. Generally, the fusion apertures 20 may be positioned anywhere along the main body 12 in order to facilitate bone growth between the sacrum and ilium and fuse the sacroiliac joint.

The distal end 22 of the fusion implant 10 may also include a tapered nose 26 which may assist in the insertion of at least the distal end 22 of the fusion implant 10 into a bone, such as the sacrum and/or ilium. The taper of the tapered nose 26 may be dimensioned such that it forms an angle between 30 degrees to 75 degrees or 40 to 60 degrees relative to the longitudinal axis $A_1$ (indicated as α in FIG. 1). However, any number of angles may be used to dimension the taper of the tapered nose 26 which may allow the tapered nose 26 to assist in inserting and implanting the fusion implant 10 across a sacroiliac joint and into the ilium and sacrum for fusion of the sacroiliac joint.

Figure 3:
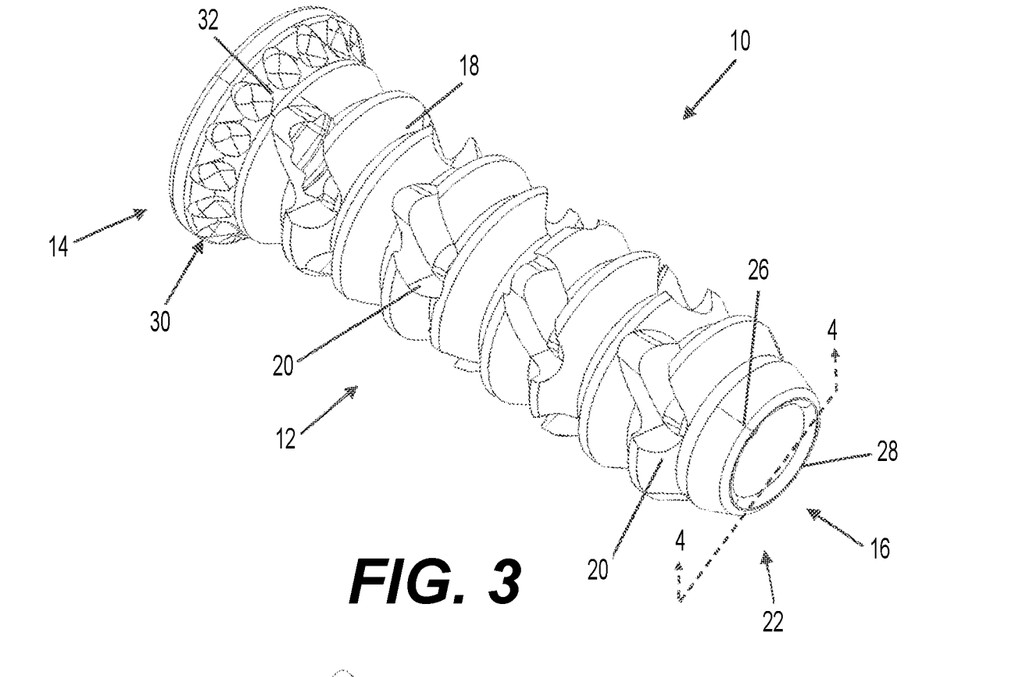
FIG. 3 illustrates a perspective view of the fusion implant of FIG. 1.
Figure 4:
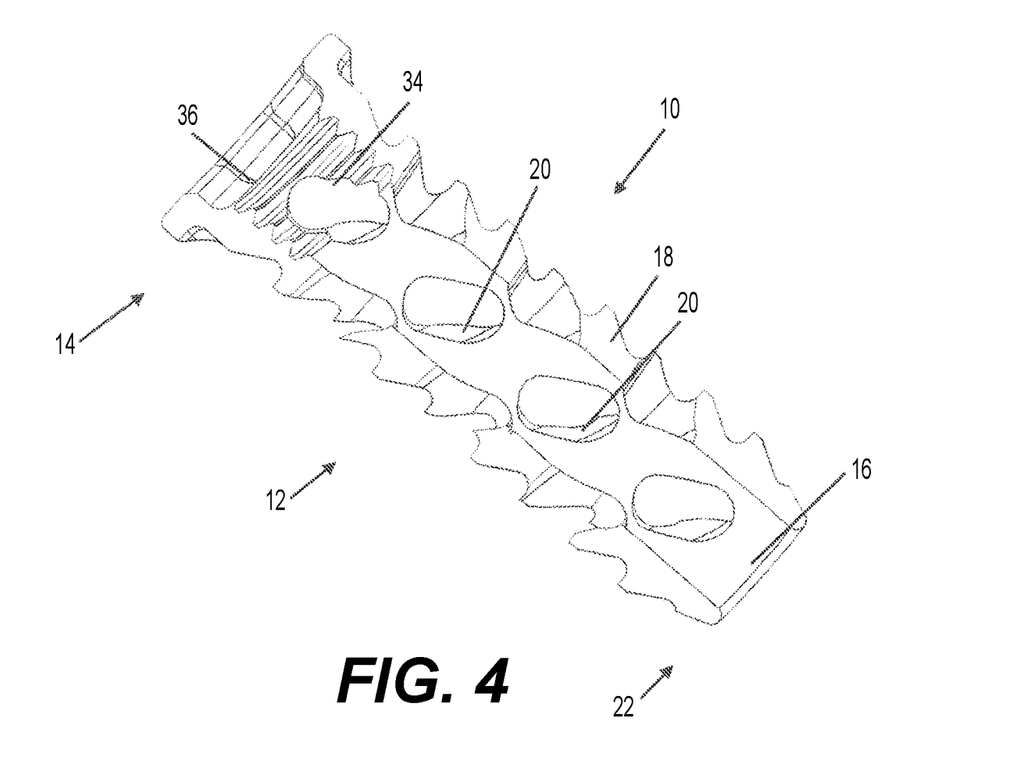
FIG. 4 illustrates a transverse cross-sectional view of the fusion implant of FIG. 1 taken along line 4-4 of FIG. 3.

As shown in FIG. 3, the distal end 22 of the fusion implant 10 may include a guide hole 28 which may assist in providing stable insertion of the fusion implant 10 along an insertion trajectory formed by, for example, an implantation tool, such as a Steinmann pin or k-wire. For example, the guide hole 28 may be shaped and dimensioned such that the guide hole 28 forms a sliding fit or a small amount of clearance over the implantation tool used to establish the insertion trajectory. This configuration may allow at least a part of the longitudinal axis $A_1$ of the fusion implant 10 to remain generally concentric with the insertion trajectory formed by the implantation tool as the fusion implant 10 travels along the insertion trajectory. In addition, this configuration may also assist in inserting and implanting the fusion implant 10 into the ilium and sacrum and across the sacroiliac joint in a desired orientation, which may result in improved surgical results and faster implantation time. By way of example, the guide hole 28 may be dimensioned such that it has a diameter that is smaller than the diameter of the through-hole 16. For instance, the guide hole 28 may have a diameter between 1 mm and 10 mm.

The proximal end 24 of the fusion implant 10 may include one or more gripping features 30 for further securing the fusion implant in an implanted position. For example, gripping features 30 may be positioned along a part of the exterior wall of the coupling head 14 such that when the fusion implant 10 is in an implanted position, at least one of the gripping features 30 may be in contact with a part of the bone to which the fusion implant 10 is implanted into, such as the ilium. By way of further example, some embodiments of the gripping features 30 may include serrated ridges, as shown in FIGS. 1 and 3, however any number of features has been contemplated and the gripping features 30 are not limited by the example embodiments provided herein. The serrated ridges may include features that provide additional grip and/or friction against the adjacent bone surface which may prevent the fusion implant 10 from rotating and/or backing out of its implanted position.

In general, the gripping features 30 may be sized and shaped such that they engage adjacent bone and assist in preventing the fusion implant 10 from rotating. Additionally, the one or more features of the gripping features 30 may allow bone to grow into the features which may further assist in securing the fusion implant 10 in its implanted position. For example, the serrated ridges of the gripping features 30 may include one or more valleys 32 which may allow a bony bridge to form from the adjacent bone and into one or more of the valleys 32. Formation of one or more bony bridges between an adjacent bone, such as the ilium, and one or more valleys 32 may further assist in preventing rotation of the fusion implant 10 relative to the adjacent bone.

In addition, the fusion implant 10 may include one or more features for assisting in coupling and decoupling the fusion implant 10 to one or more insertion instruments. For example, a threaded feature 34 may extend along at least a part of the inner wall of the through-hole 16. The threaded feature 34 may allow an instrument to releasably couple to the fusion implant 10, such as for positioning and implanting the fusion implant 10 across a sacroiliac joint of a patient, as will be described in greater detail below.

Furthermore, the fusion implant 10 may include one or more counter-torque features 36 which may assist in, for example, decoupling the fusion implant 10 from one or more insertion instruments. More specifically, and as shown by way of example in FIGS. 2 and 4, the coupling head 14 may have a counter-torque feature 36 including an octagonal cavity. The octagonal cavity of the counter-torque feature 36 may be sized and shaped to allow at least a part of a counter-torque instrument to couple to the counter-torque feature 36 in order to assist in preventing the fusion implant 10 from rotating during at least one of coupling and decoupling of the fusion implant 10 from an insertion instrument, as will be described in greater detail below. Although shown by way of example as an octagonal cavity, the counter-torque feature 36 may be any shape, such as hexagonal or square, necessary for mating with at least a part of the insertion instrument and assisting in providing counter-torque without departing from the scope of this disclosure. Furthermore, any number of features may be incorporated into the fusion implant 10 for assisting in the coupling and decoupling of the fusion implant 10 to one or more insertion instruments without departing from the scope of this disclosure.

Figure 5:
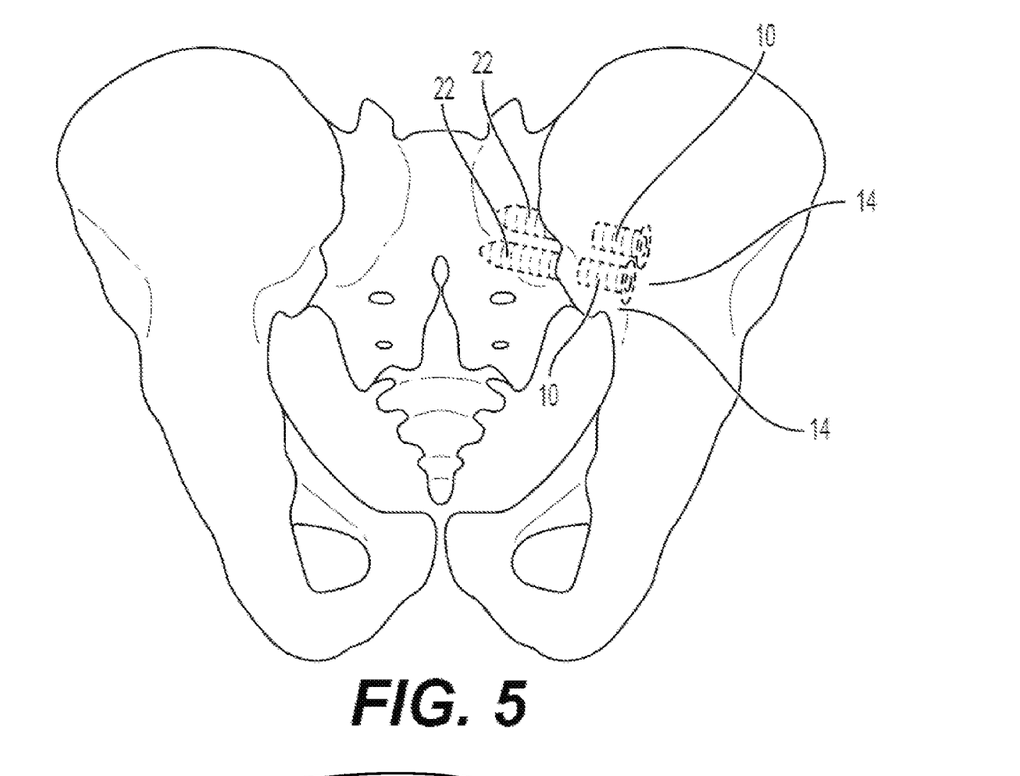
FIG. 5 illustrates a front view of a pelvic region of a human skeleton showing the fusion of a sacroiliac joint by way of fixation of two fusion implants across the sacroiliac joint and secured to both the sacrum and ilium.
Figure 6:
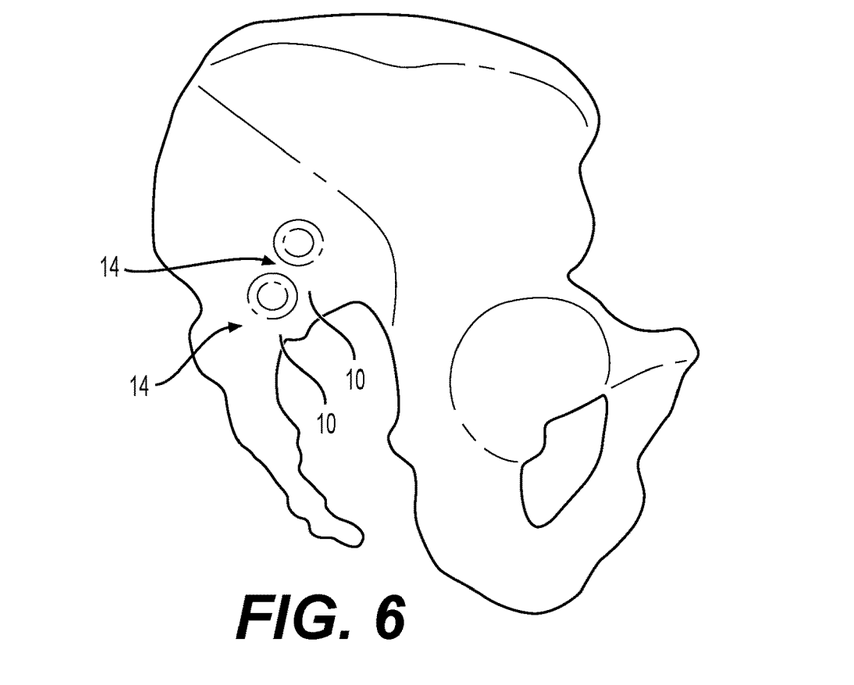
FIG. 6 illustrates a side view of the pelvic region of the human skeleton of FIG. 5 showing the proximal end of the fusion implants.

FIGS. 5 and 6 illustrate an example of the implantation of a pair of fusion implants 10 across the sacroiliac joint and secured into the sacrum and ilium. The proximal ends 24 of the fusion implants 10, which includes at least a part of the coupling head 14, is shown as extending from the ilium.

Additionally. FIG. 5 shows at least part of the distal ends 22 of the fusion implants 10 secured into the sacrum. Both of the fusion implants 10 shown in FIGS. 5 and 6 were inserted through the ilium, across the sacroiliac joint and secured into the sacrum in order to secure the positioning of the ilium relative to the sacrum and assist in fusing the sacroiliac joint. One or more fusion implants, such as two or three fusion implants 10, may be implanted across a single sacroiliac joint for assisting in fusing the sacroiliac joint. Example methods of implantation and insertion instruments for implanting one or more fusion implants will be discussed in greater detail below.

FIGS. 7-12 illustrate an example embodiment of an insertion device 40 wherein at least a part of the insertion device 40 is coupled to an embodiment of a fusion implant 110. The insertion device 40 may include an inner shaft 42 coupled to an outer shaft 44 wherein the inner shaft 42 may be able to rotate and translate along a longitudinal axis $A_2$ of the insertion device 40 independent of the outer shaft 44. Additionally, at least one of the inner shaft 42 and outer shaft 44 may have a coupling feature for assisting in securing the fusion implant 110 to the insertion device 40. Furthermore, at least one of the inner shaft 42 or outer shaft 44 may have a counter-torque feature for assisting in coupling and/or decoupling the insertion device 40 to the fusion implant 110. Although the insertion device 40 is described herein as being coupled to the fusion implant 110 of the current example embodiment, the insertion device 40 may be coupled to at least any of the fusion implant 10, 110, 210 example embodiments disclosed herein without departing from the scope of this disclosure. Additionally, any of the features or functions described with respect a particular embodiment of the insertion device and/or fusion implant may be incorporated in at least any of the other example embodiments of the insertion devices and/or fusion implants, respectively, described herein without departing from the scope of this disclosure. Therefore, like numbers may be used to reference the same or similar features across various embodiments described herein.

Figure 9:
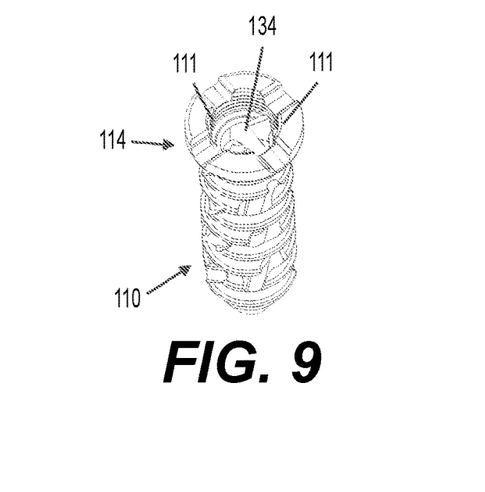
FIG. 9 is a perspective view of the fusion implant of FIG. 7.

Prior to implantation of the fusion implant 110, the insertion device 40 may be coupled to the fusion implant 110. For instance, the outer shaft 44 of the insertion device 40 may include one or more extensions 48 extending from the distal end 50 of the outer shaft 44 which may engage and releasably couple to one or more indentations 111 along the coupling head 114 of the fusion implant 110, as shown in FIG. 9. The extensions 48 may include any number of features that may form a sliding fit with the indentions 111 of the coupling head 114. (All other features of fusion implant 110 pictured but not specifically described herein are identical to those features described with respect to fusion implant 10 and will not be repeated here). However, the outer shaft 44 may have any number of features for releasably engaging the fusion implant 110 without departing from this disclosure.

Additionally, the extensions 48 of the outer shaft 44 may engage the fusion implant 110 and provide counter-torque during coupling and decoupling of the inner shaft 42. For example, once the extensions 48 of the outer shaft 44 are engaged with the indentations Ill of the fusion implant 110, the distal end 56 of the inner shaft 42 may be lead through the through-hole 54 of the outer shaft 44 and into the threaded coupling feature 134 of the fusion implant 110. The distal end 56 of the inner shaft 42 may include one or more threads 60 which may allow the inner shaft 42 to threadably engage the threaded coupling feature 134 of the fusion implant 110. As described above, the inner shaft 42 may rotate and translate along the longitudinal axis $A_2$ of the insertion device 40 independent of the outer shaft 44. Therefore, the user of the insertion device 40 may secure the rotational positioning of the outer shaft 44 and rotate the inner shaft 42 clockwise relative to the outer shaft 44 while threadably engaging the threads 60 of the inner shaft 42 to the threaded coupling feature 134 of the fusion implant 110. In this configuration, the outer shaft 44 may provide the counter-torque necessary for the inner shaft 42 to threadably engage the fusion implant 110 and releasably secure the fusion implant 110 to the insertion device 40 for implantation across a sacroiliac joint of a patient. By way of example, the inner shaft 42 may continue to threadably engage the threaded coupling feature 134 of the fusion implant 110 until a proximal enlarged portion 62 of the inner shaft 42 mates against a proximal end 52 of the outer shaft 44. In general, mating of the proximal enlarged portion 62 with the proximal end 52 of the outer shaft 44 may prevent the inner shaft 42 from continuing to travel along the longitudinal axis $A_2$ independent of the outer shaft 44.

Figure 10:
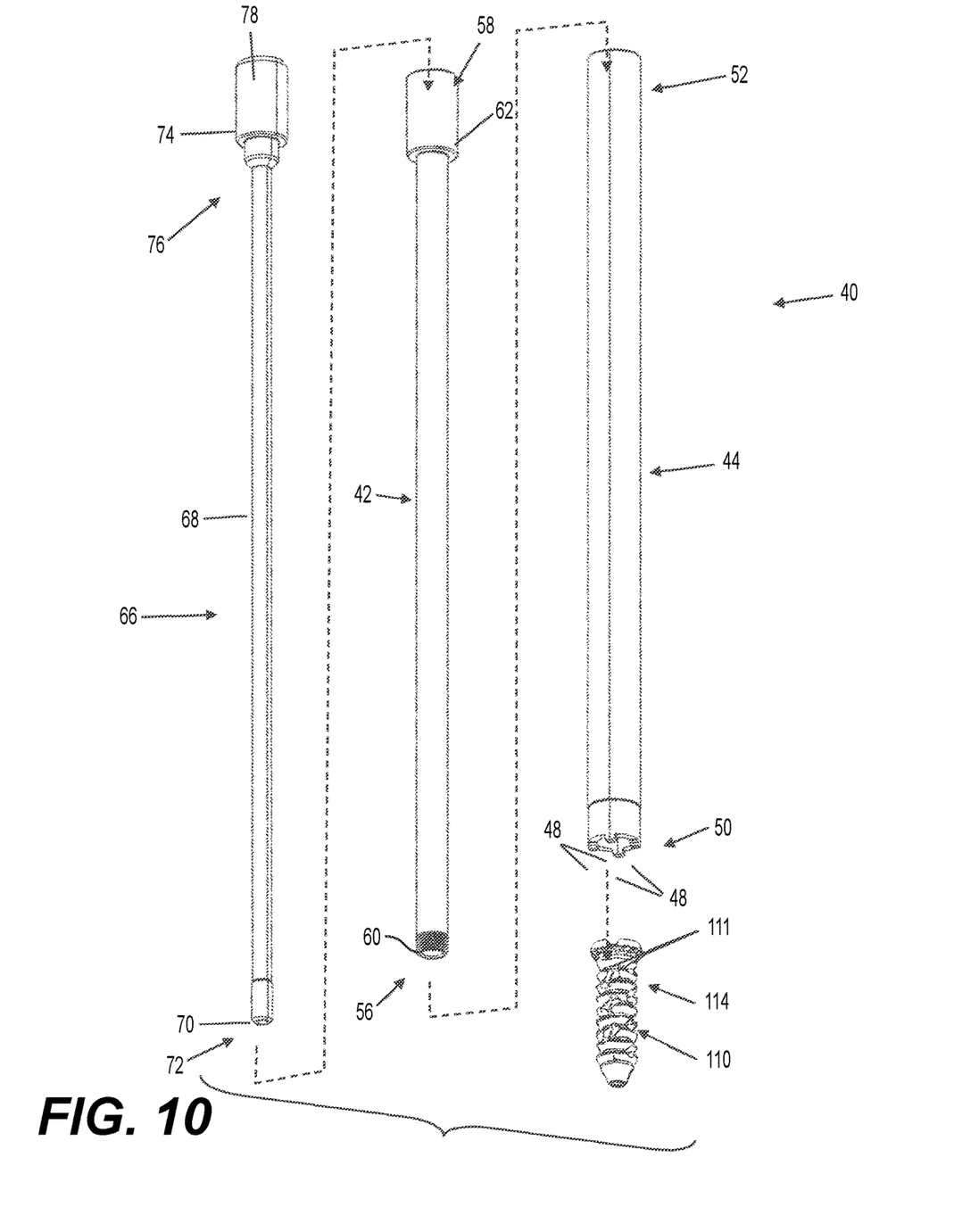
FIG. 10 illustrates an exploded view of the sacroiliac fusion system of FIG. 7.

The insertion device 40 may further include additional features and/or components for assisting in inserting and preparing the fusion implant 110. As shown in FIG. 10, the insertion device 40 may include a pusher 66 which may be used to deposit fusion-promoting material into the fusion implant 110, such as into the through-hole 116, before, during or after implantation of the fusion implant 110. The pusher 66 may include an elongated shaft 68 with a head 70 located at the distal end 72 of the elongated shaft 68. The elongated shaft 68 and head 70 may be sized and shaped such that they are able to travel through at least part of an inner lumen 64 of the inner shaft 42, wherein the lumen 64 may extend through the entire length of the inner shaft 42.

An example method of use of the pusher 66 may include the steps of first coupling the outer shaft 44 and inner shaft 42 to the fusion implant 110. Once both the outer shaft 44 and inner shaft 42 have been securely coupled to the fusion implant 110, fusion-promoting material may be inserted into the lumen 64 of the inner shaft 42 prior to, during or after implantation of the fusion implant 110. The distal end 152 of the pusher 66, or the head 70, may then be inserted into lumen 64 of the inner shaft 42 and advanced through the length of the inner shaft 42. The lumen 64 of the inner shaft 42 may extend through the length of the inner shaft 42 such that advancement of the head 70 of the pusher 66 through the lumen 64 may eventually force the fusion-promoting material out of the lumen 64 and into the fusion implant 110, such as into the through-hole 116. The head 70 of the pusher 66 may be sized and shaped to efficiently and effectively force at least a majority of the fusion-promoting material through and out the distal end 56 of the inner shaft 42 in order to reduce wasting the fusion promoting material.

Additionally, prior to implantation of the fusion implant 110, the head 70 of the pusher 66 may be used to insert fusion-promoting material into the fusion implant 110 either before or after the fusion implant 110 is removably coupled to any part of the insertion device 40, such as the inner shaft 42 or outer shaft 44. In addition, the pusher 66 may include a proximal enlarged portion 74 at a proximal end 76 of the elongated shaft 68. Furthermore, the proximal enlarged portion 74 may be positioned relative to the head 70 of the pusher 66 such that the proximal enlarged portion 62 limits the travel of the head 70 relative to at least the fusion implant 110 coupled to the insertion device 40. For example, the proximal enlarged portion 74 may be positioned relative to the head 70 of the pusher 66 such that the head 70 may not travel, or at least a minimal distance, into the through-hole 116 due to the proximal enlarged portion 74 of the pusher 66 mating against the proximal enlarged portion 62 of the inner shaft 42, as shown by way of example in FIG. 11. This configuration may assist in minimizing the amount of fusion-promoting material the head 70 of the pusher 66 may be able to push out of the fusion implant 110 which may increase the effectiveness of the fusion-promoting material in forming a bony bridge at least across the fusion implant 110.

As discussed above, fusion within the sacroiliac joint may be facilitated or augmented by introducing or positioning various fusion-promoting materials within and/or adjacent to the fusion implant 110. Such materials may be introduced before, during, or after the insertion of the fusion implant and may include, but are not necessarily limited to, autologous bone harvested from the patient, bone allograft, mesenchymal-stem-cell-based-products (e.g. Osteocel® Plus), bone xenograft, any number of non-bone implants (e.g. ceramic, metallic, polymer), bone morphogenic protein, and bio-resorbable compositions including but not limited to any of a variety of poly (D, L-lactide-co-glycolide)-based polymers.

The proximal end 76 of the pusher 66 may include a blunt feature 78, such as a blunt proximal end 76 of the proximal enlarged portion 74, which may be favorable for impacting with a mallet or other tool for assisting in implanting the fusion implant 110. In addition, the proximal end 58 or proximal enlarged portion 62 of the inner shaft 42 may include a blunt feature, such as a blunt proximal end 58, which may also be favorable for impacting with a mallet or other tool for assisting in implanting the fusion implant 110.

In addition, the pusher may include a guide lumen 80 that may assist in providing a stable insertion of the fusion implant 110 along an insertion trajectory formed by an implantation tool, such as a Steinmann pin or k-wire. For example, the guide lumen 80 may be shaped and dimensioned such that the guide lumen 80 forms a sliding fit or a small amount of clearance over the implantation tool used to establish the insertion trajectory. This configuration may allow a more stable delivery and implantation of the fusion implant 110 which may result in improved ease of use of the insertion device 40 along the insertion trajectory and faster implantation time. Furthermore, the guide lumen 80 may be dimensioned such that it has a diameter that is similar or equal in shape and dimension to the guide hole 128 of the fusion implant 110.

An example method of preparing the fusion implant 110 to the insertion device 40 and permanently implanting the fusion implant may include at least some of the steps described below. For example, a user may prepare the fusion implant 110 by inserting one or more fusion-promoting materials into the through-hole 116. In addition, the head 70 of the pusher 66 may be used to push the fusion-promoting material into the through-hole 116, as described above. The extensions 48 of the outer shaft 44 may then be coupled to the indentations 111 of the fusion implant 110 prior to advancing the distal end 56 of the inner shaft 42 through the through-hole 54 of the outer shaft 44 and towards the threaded coupling feature 134 of the fusion implant 110. The user may then secure the rotational positioning of the outer shaft 44 relative to the inner shaft 42 while threadably engaging the one or more threads 60 of the inner shaft 42 with the threaded coupling feature 34. In this arrangement, the outer shaft 44 may provide the necessary counter-torque to the torque generated from threadably engaging the threads 60 of the inner shaft 42 into the threaded coupling feature 134 of the fusion implant 110. Once the inner shaft 42 and outer shaft 44 have been coupled to the fusion implant 110, the pusher 66 may be used to insert fusion-promoting material into the lumen 64 of the inner shaft 42. Additionally, the pusher 66 may be used to further push the fusion-promoting material through the lumen 64 and into the fusion implant 110, such as into the through-hole 116.

An implantation trajectory and pilot hole for at least one fusion implant 110 may be prepared by inserting a needle or stylet into the ilium, across the sacroiliac joint, and into the sacrum. A k-wire may then be placed through the needle in order to provide the insertion trajectory for the fusion implant 110. A space around the k-wire may be formed with the use of one or more dilators. In addition, one or more drills, reamers or taps may be used to prepare insertion holes in the ilium and sacrum for implanting the fusion implant 110 across the sacroiliac joint and into the ilium and sacrum. Additional tools may be used to prepare the sacroiliac joint for promoting fusion, such as tools that may disrupt the cartilage in the sacroiliac joint in order to create some bone-on-bone contact between the ilium and sacrum along at least a part of the sacroiliac joint.

Figure 7:
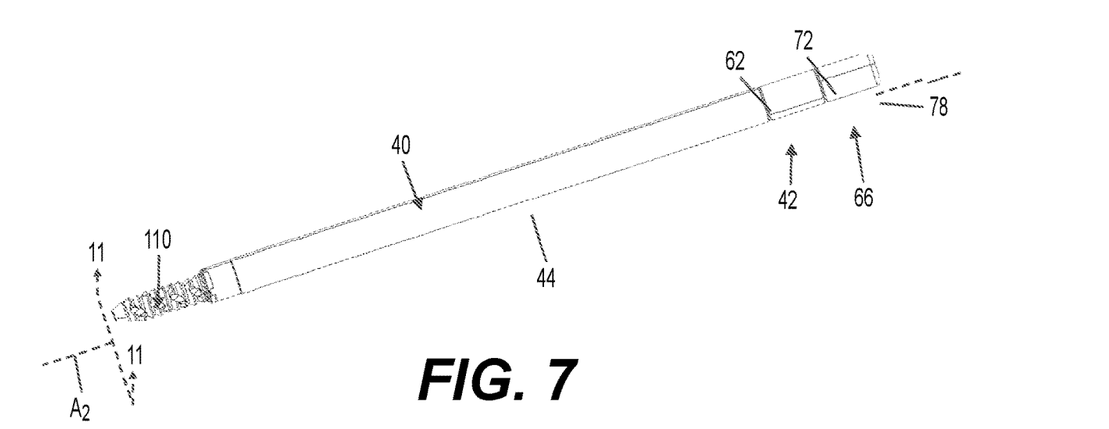
FIG. 7 illustrates an embodiment of a sacroiliac fusion system including another example of a fusion implant releasably coupled to an insertion device.
Figure 8:
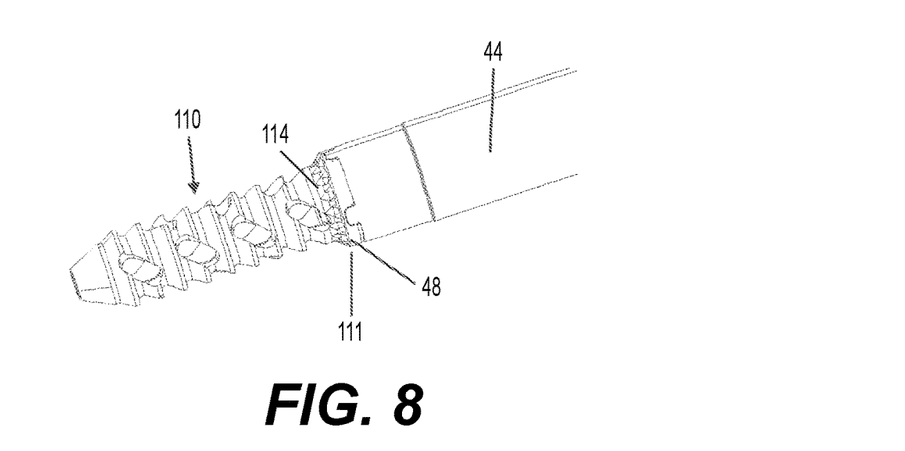
FIG. 8 illustrates an enlarged view of the sacroiliac fusion system of FIG. 7 including the fusion implant and distal portion of the insertion device.
Figure 11:
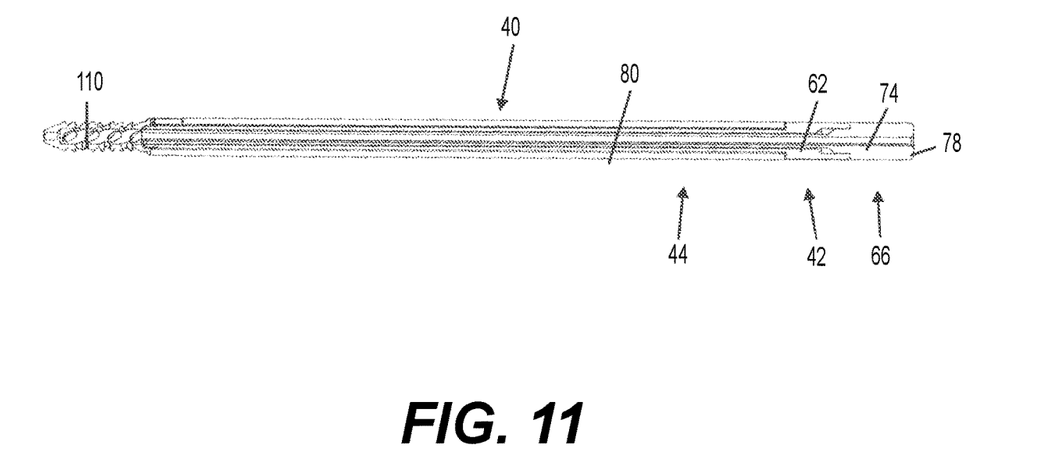
FIG. 11 illustrates a transverse cross-sectional view of the sacroiliac fusion system of FIG. 7 taken across line 11-11 of FIG. 7.
Figure 12:
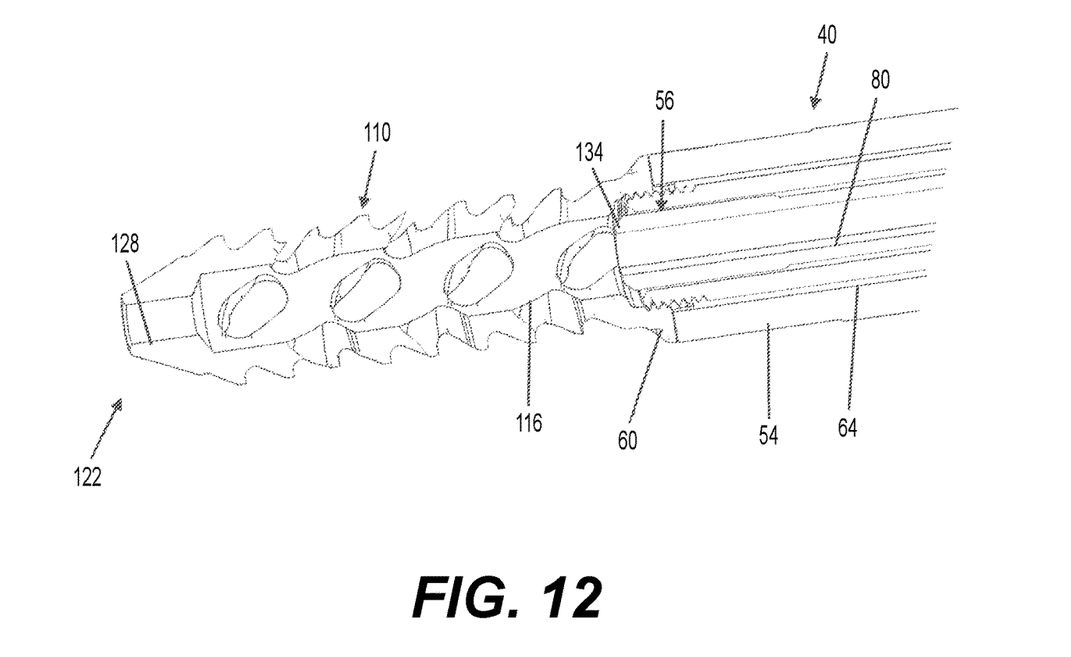
FIG. 12 illustrates an enlarged transverse cross-sectional view of the sacroiliac fusion system of FIG. 11 including the fusion implant and distal portion of the insertion device.

The proximal end of the insertion trajectory, such as the proximal end of the k-wire, may be lead through the guide hole 128 of the fusion implant 110 and along the guide lumen 80 of the pusher 66, wherein the pusher 66 is releasably coupled to the inner shaft 42 and outer shaft 44 as shown by way of example in FIGS. 7 and 11. Both the guide hole 128 and the guide lumen 80 may be sized and shaped such that the implantation tool, or k-wire, may have minimal clearance in order to prevent misalignment of the fusion implant 110 during implantation of the fusion implant 110. The user may advance the insertion device 40 with the attached fusion implant 110 along the insertion trajectory until the distal end 122 of the fusion implant 110 is introduced to an insertion hole formed in the ilium. The user may then use a mallet or other tool to apply a force upon the blunted feature 78 of the pusher 66 until the distal end 122 of the fusion implant 110 has been inserted across the sacroiliac joint and into the sacrum. Once the fusion implant 110 is in the desired implanted position, the user may decouple the pusher 66 from at least the inner shaft 42 and place additional fusion-promoting material into the lumen 64 of the inner shaft 42. The user may then use the pusher 66 to push the fusion-promoting material into the fusion implant 110 by advancing the head 70 of the pusher 66 through the lumen 64, as described above.

Once the fusion implant 110 has been implanted and prepared for permanent implantation, the user may decouple the insertion device 40 from the fusion implant 110 by, for example, removing the pusher 66 and securing the rotational position of the outer shaft 44 while rotating the inner shaft 42 in a counter-clockwise direction. Securing the rotational position of the outer shaft 44 while rotating the inner shaft 42 in a counter-clockwise direction allows the outer shaft 44 to provide the counter-torque necessary to allow the threads 60 of the inner shaft 42 to disengage the threaded coupling feature 134 of the fusion implant 110 without disrupting the fusion implant 110, such as causing the fusion implant 110 to rotate. Once the inner shaft 42 is disengaged from the fusion implant 110, the user may then disengage the extensions 48 of the outer shaft 44 from the indentations 111 of the fusion implant 110. After the fusion implant 110 has been completely disengaged from the insertion device 40, the fusion implant 110 may remain permanently implanted in the patient.

Figure 13:
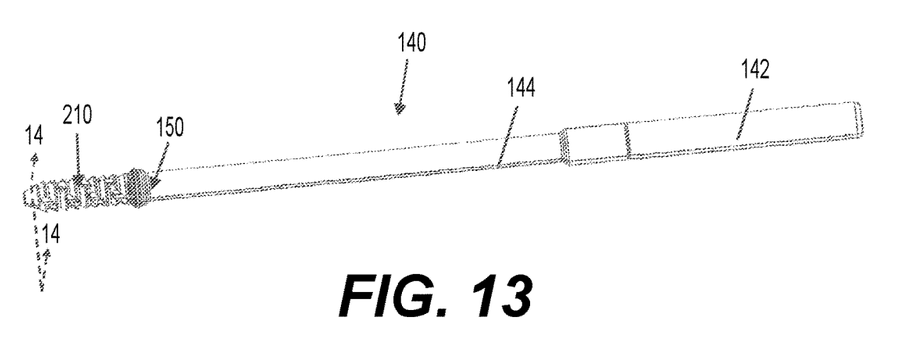
FIG. 13 illustrates another embodiment of a sacroiliac fusion system including a fusion implant and an insertion device.
Figure 14:
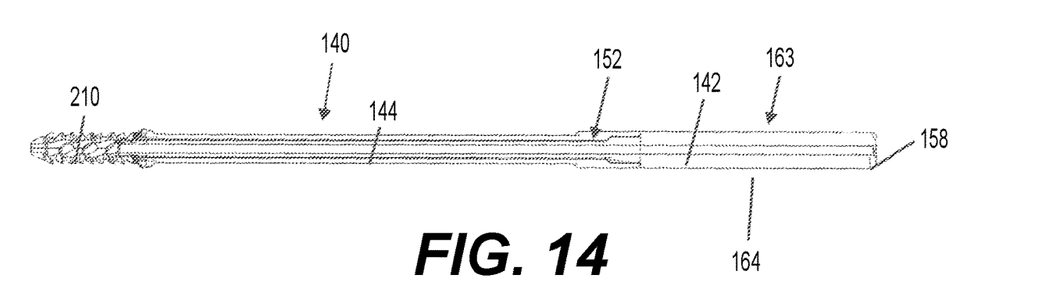
FIG. 14 illustrates a transverse cross-sectional view of the sacroiliac fusion system of FIG. 13 taken across line 14-14 of FIG. 13.
Figure 15:
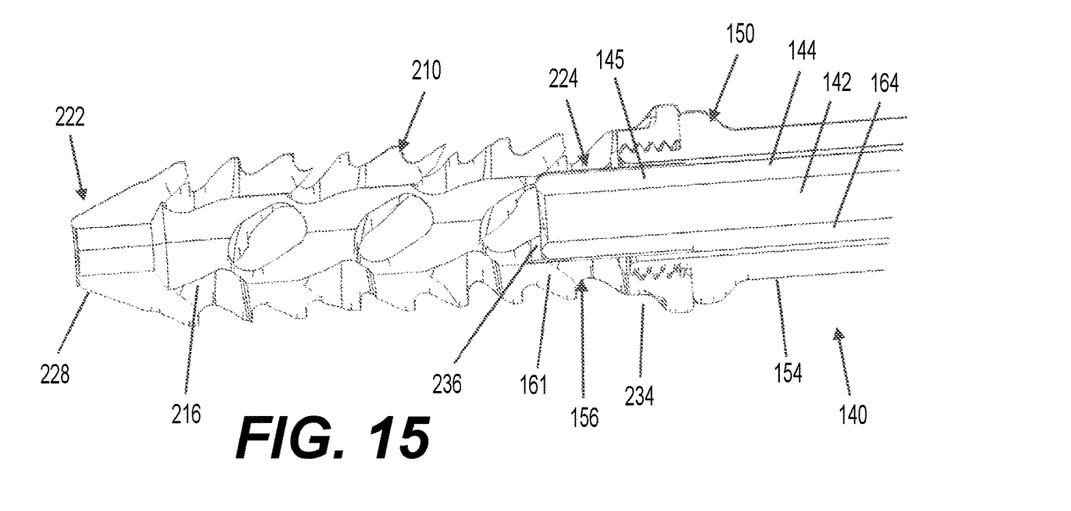
FIG. 15 illustrates an enlarged transverse cross-sectional view of the sacroiliac fusion system of FIG. 14 including the fusion implant and distal portion of the insertion device.
Figure 16:
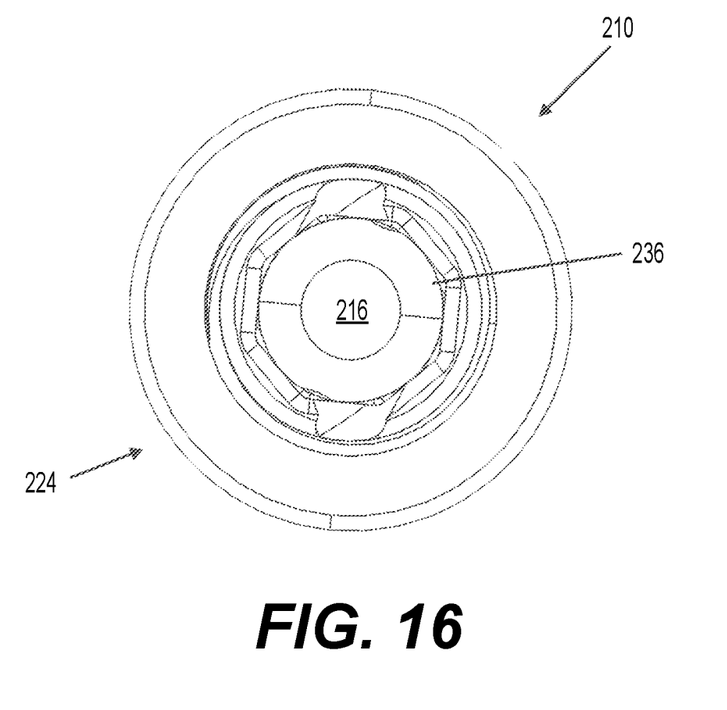
FIG. 16 illustrates a top view of the fusion implant of FIG. 13 showing the through-hole extending through the fusion implant which may be packed with a fusion-promoting material.
Figure 17:
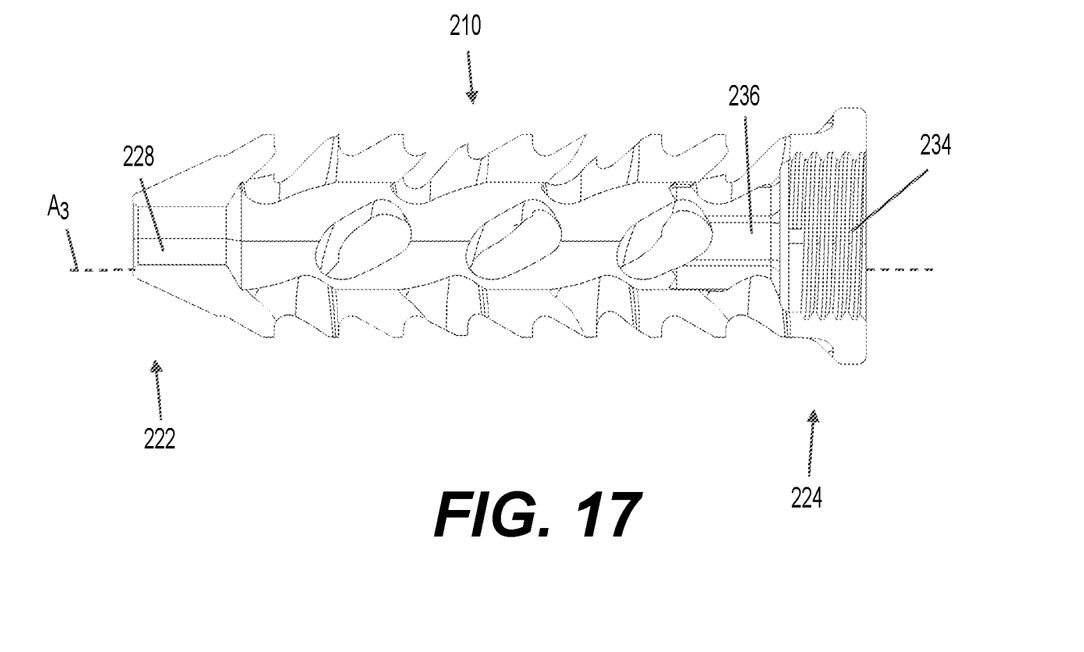
FIG. 17 illustrates a transverse cross-sectional view of the implant of FIG. 14.

Additional embodiments of the insertion device and fusion implant have been contemplated and are discussed in greater detail below by way of example. For instance, FIGS. 13-17 illustrate another example embodiment of an insertion device 140 and another example embodiment of a fusion implant 210, with FIGS. 13-15 showing an example of the fusion implant 210 releasably coupled to the insertion device 140. The insertion device 140 may include an outer shaft 144 and an inner shaft 142 with the inner shaft 142 having features that may allow it to provide similar functions as the pusher 66 described above.

The outer shaft 144 of the insertion device 140 may include threaded features 145 along its distal end 150 which may threadedly engage a threaded coupling feature 234 of the fusion implant 210. Additionally, the outer shaft 144 may include a through-hole 154 that extends the length of the outer shaft 144 and which may be sized and shaped to allow at least the distal end 156 of the inner shaft 142 to travel along the length of the through-hole 154. For instance, the distal end 156 of the inner shaft 142 may be inserted into the through-hole 154 of the outer shaft 144 and forced to travel along the length of the through hole 154 until the distal end 156 mates with a counter-torque feature 236 embedded within a part of the proximal end 224 of the fusion implant 210, as shown by way of example in FIG. 15. Furthermore, the distal end 156 of the inner shaft 142 may have one or more counter-torque features 161 that allow it to releasably couple to the counter-torque feature 236 in the fusion implant 210. For example, the distal end 156 of the inner shaft 142 may have a counter-torque feature 161 including an octagonally extruded tip that may releasably couple to an octagonal recess of the counter-torque feature 236 in the fusion implant 210. Additionally, the octagonal recess may be continuous with the through-hole 216 of the fusion implant 210. Although the counter-torque features of the fusion implant and inner shaft have been described by way of example as having an octagonal shape, any number of shapes and sizes may be used without departing from the scope of this disclosure.

The method of preparation of the fusion implant 210 and implantation site, including the insertion trajectory, may include some or all of the same or similar steps described above for the insertion device 40 and fusion implant 10, 110 and will not be repeated again here for sake of brevity. After the fusion implant 210 and implantation site have been prepared and the fusion implant 210 has been coupled to both the outer shaft 144 and inner shaft 142, the proximal end of the insertion trajectory, such as the proximal end of a k-wire, may be lead through the guide hole 228 of the fusion implant 210 and along the lumen 164 of the inner shaft 142. Both the guide hole 228 and the lumen 164 of the inner shaft 142 may be sized and shaped such that the insertion trajectory, or k-wire, may have minimal clearance in order to prevent misalignment of the fusion implant 210 during implantation of the fusion implant 210. For example, the user may advance the insertion device 140 with the attached fusion implant 210 along the insertion trajectory until the distal end 222 of the fusion implant 210 is introduced to an insertion hole formed in the ilium. The user may then use a mallet or other tool to apply a force upon a blunted feature or blunt end 158 of the inner shaft 142 until the distal end 222 of the fusion implant 210 has been inserted across the sacroiliac joint and into the sacrum and ilium. Once the fusion implant 210 is in the desired implanted position, the user may then place additional fusion-promoting material into the fusion implant 210. This may be accomplished by removing the inner shaft 142 and inserting fusion-promoting material into the through hole 154 of the outer shaft 144. Once fusion-promoting material has been placed in the through hole 154, either the distal end 156 of the inner shaft 142 or the distal end 72 of a pusher, for example such as the pusher 66 described above, may be used to push the fusion-promoting material through the through hole 154 and into the fusion implant 210.

Once the fusion implant 210 has been implanted and prepared for permanent implantation, the user may decouple the insertion device 140 from the fusion implant 210 by, for example, securing the rotational position of the inner shaft 142 while rotating the outer shaft 144 in a counter-clockwise direction. Securing the rotational position of the inner shaft 142 while rotating the outer shaft 144 in a counter-clockwise direction allows the inner shaft 142 to provide the counter-torque necessary to allow the threaded feature 145 of the outer shaft 144 to disengage the threaded coupling feature 234 of the fusion implant 210 without disrupting the position of the fusion implant 210, such as preventing the fusion implant 210 from rotating. Furthermore, and shown by way of example in FIG. 16, the counter-torque feature 236 may extend along a longitudinal axis $A_3$ of the fusion implant 210 a greater distance than the threaded coupling feature 234 extends along the longitudinal axis $A_3$. Therefore, as the outer shaft 144 disengages and translates away from the fusion implant 210, the counter-torque feature 161 of the inner shaft 142 may slide along the counter-torque feature 236 of the fusion implant 210 until the outer shaft 144 is completely disengaged from the fusion implant 210. This configuration ensures that the inner shaft 142 may continue to provide the necessary counter-torque while the outer shaft 144 is disengaging from the fusion implant 210 so that the placement of the fusion implant 210 is not disrupted. One or more features along the proximal end 163 of the inner shaft 142 and proximal end 152 of the outer shaft may interact such that movement of one of the inner shaft 142 or outer shaft 144 may result in movement, such as linear translation, of the other.

Once the outer shaft 144 is disengaged from fusion implant 210, the user may then disengage the distal end 156 of the inner shaft 142 from the counter-torque feature 236 of the fusion implant 210. After the fusion implant 210 has been completely disengaged from the insertion device 140, the fusion implant 210 may remain permanently implanted in the patient.

With regard to the above detailed description, like reference numerals used therein may refer to like elements that may have the same or similar dimensions, materials, and configurations. While particular forms of embodiments have been illustrated and described, it will be apparent that various modifications can be made without departing from the spirit and scope of the embodiments herein. Accordingly, it is not intended that the invention be limited by the forgoing detailed description.

When creating an access surgical corridor through the ilium, sacroiliac joint, and sacrum, the surgical access system may come in close proximity to motor nerves, sensory nerves, and mixed nerves. For example, the surgical access system may come in close proximity with L4, L5, and S1 nerves. Inadvertent contact with these nerves, even if transient could lead to pain, numbness, parasthesias, or other nerve injuries. As such, information regarding the proximity, health, and/or status of these sensitive tissues is desirable. Additionally, it is advantageous that such information be presented in a robust and expeditious manner.

A neurophysiologic monitoring system may perform nerve proximity, health, and/or status testing on one or more nerves as the fusion implant is placed across the sacroiliac joint. One example of a suitable neuromonitoring system is found in commonly owned U.S. Pat. No. 8,255,045, issued Aug. 28, 2012 and entitled "Neurophysiology Monitoring System" (incorporated by reference).

According to one embodiment, the neurophysiologic monitoring system includes a means for stimulating the nerves that lie near the surgical access corridor. By way of example, this may include electrifying k-wires, pins, dilators, drills, broaches, screws, and/or any other instrument or hardware before, during, or after introduction into the surgical access corridor. According to one implementation, this may be performed using a stimulation clip in electrical communication with the control unit of the neuromonitoring system. According to another implementation, various instruments may be insulated to reduce or eliminate the amount of current shunting to nearby tissues. The neurophysiologic monitoring system also includes a means for recording neuromuscular responses (via electromyography (EMG) or mechanomyography (MMG)) elicited in response to the stimulation. By way of example only, the EMG responses may be recorded from the vastus lateralis, tibialis anterior, medial gastrocnemius, and biceps femoris muscles. According to one implementation, the EMG responses recorded are for the limb ipsilateral to the operative side. According to another implementation, the EMG responses recorded are for both the ipsilateral and contralateral limbs. By way of example only, the recording parameters are those set forth in the above-referenced '045 patent (incorporated by reference) with respect to threshold-based pedicle screw testing.

The neurophysiologic monitoring system includes a means for ascertaining the stimulation threshold intensities required to elicit a response from one or more muscle groups. The amount of current required to elicit a significant neuromuscular response ($I_{Thresh}$) may then be calculated for each response. $I_{Thresh}$ provides a measure of the communication between the stimulation (associated with the k-wire, pin, dilator, drill, broach, screw, etc.) and the nerve. According to one or more implementations, the threshold hunting algorithm is used to quickly find $I_{Thresh}$ using a bracketing and bisection method. The bracketing method quickly finds a range (bracket) of stimulation currents that must contain $I_{Thresh}$ and the bisection method narrows the bracket until $I_{Thresh}$ is known in within a specified accuracy. In another such implementation, the threshold hunting algorithm may begin by immediately determining an appropriate safety level and entering the bracketing phase by initiating stimulation at one or more boundary current levels. Once the safety level is known, the algorithm may transition to the bracketing and bisection phases to determine the actual $I_{Thresh}$ value. The algorithms described in brief detail above for finding $I_{Thresh}$ for a compound nerve may be similar to that shown and described in more detail in the above-referenced '045 patent (incorporated by reference) for finding $I_{Thresh}$ on a motor nerve.

According to one embodiment, there is provided a means for identifying the health and/or status of the nearby nerves based on the threshold stimulation current intensities acquired as described above. By way of example only, a response greater than a first predetermined threshold (ex: 40 mA) would generally be "safe"; a response below a separate predetermined threshold (ex: 20 mA) would generally be "unsafe"; and any response between the first and second thresholds would be cautionary. According to one implementation, there may be different predetermined thresholds based on the anatomy being traversed (ex: ilium, sacroiliac joint capsule, sacrum).

According to a preferred method, the neuromonitoring system elicits and records neuromuscular responses after positioning of one or more instruments or hardware (e.g., k-wires, pins, dilators, drills, broaches, screws, etc.) or dynamically as the instrument or hardware is being placed. The neurophysiologic monitoring system may quickly and accurately determine this data and convey the useful information in a simple and easily comprehensible manner for interpretation by a surgeon, neurophysiologist, or other medical personnel. It is contemplated that the control unit of the neuromonitoring system may automatically ascertain this information (for example, using one of the threshold hunting algorithms disclosed above) and/or communicate any of numerical, graphic, audio, and visual feedback corresponding to one or more of these findings. Armed with this useful information, the surgeon may detect a problem or potential problem and then act to avoid and/or mitigate the problem.

Modifications may be made to the foregoing embodiments without departing from the basic aspects of the inventions described herein. Although the embodiments of the invention may have been described in substantial detail with reference to one or more specific embodiments, changes may be made to the embodiments specifically disclosed in this application, yet these modifications and improvements are within the scope and spirit of this disclosure.

Certain embodiments of the invention are set forth in the claim(s) that follow(s).

What is claimed is:

1. A method of fusing a sacroiliac joint, comprising:
securing a fusion implant to a distal end of an insertion device, wherein the fusion implant includes: a main body having a longitudinal axis and a length extending from a proximal end to a distal end and being dimensioned for placement across a sacroiliac joint, the main body having a plurality of anti-migration features disposed along at least a portion of the length of the main body; a guide hole extending through the longitudinal axis of the main body; a plurality of fusion apertures located along a substantial portion of the length of the main body, the substantial portion of the length of the main body including at least a portion of the length of the main body having anti-migration features, and wherein at least one of the plurality of fusion apertures extends into the main body through at least one of the plurality of anti-migration features; and a coupling head disposed at the proximal end of the fusion implant, the coupling head having anti-rotation features on its external surface configured for bone to grow into the anti-rotation features and secure the implant in position;
attaching the insertion device to the coupling head for inserting the fusion implant across a sacroiliac joint, wherein the insertion device further includes an inner shaft coupled to an outer shaft, where the inner shaft can rotate and travel along a longitudinal axis of the insertion device independently of the outer shaft, and wherein the inner shaft includes a lumen that extends along the entire length of the inner shaft and configured to allow the head of a pusher to travel along the length of the lumen;
inserting the fusion implant across the sacroiliac joint and into a sacrum and ilium; and
releasing the insertion device from the fusion implant.

2. The method of claim 1, including the step of inserting fusion-promoting material in the fusion implant prior to implantation.

3. The method of claim 1, including the step of inserting fusion-promoting material in the fusion implant after the fusion implant is implanted across the sacroiliac joint and into the sacrum and ilium.

4. The method of claim 3, including the step of pushing fusion-promoting material into the fusion implant using the pusher.

5. The method of claim 1, including the step of inserting the fusion implant through the ilium, across the sacroiliac joint, and then into the sacrum.

6. The method of claim 1, including the step of implanting a second fusion implant across the sacroiliac joint for fusion of the sacroiliac joint.

7. The method of claim 1, wherein the insertion device further includes the pusher configured for pushing fusion-promoting material into the fusion implant.

8. The method of claim 7, the insertion device includes:
   the inner shaft having an inner shaft proximal end and an inner shaft distal end, with the inner shaft distal end having at least one thread for engaging the coupling head of the fusion implant;
   the outer shaft having an outer shaft proximal end and an outer shaft distal end, with the outer inner shaft distal end having at least one counter-torque feature for engaging a fusion implant counter-torque feature implant; and
   the pusher having a pusher proximal end and a pusher distal end, with the pusher distal end including a head configured for pushing fusion-promoting material into the fusion implant.

9. The method of claim 8, wherein the at least one counter-torque feature of the outer shaft includes extensions extending from the outer shaft distal end and the extensions mate with indentations along the fusion implant configured for providing counter-torque.

10. The method of claim 7, wherein the pusher includes a blunted feature along the proximal end of the pusher and a guide lumen that extends along the length of the pusher.

11. The method of claim 1, wherein each of the plurality of fusion apertures includes an elongated shape.

12. The method of claim 11, wherein the elongated shape of the plurality of fusion apertures is disposed diagonally with respect to the longitudinal axis of the main body.

13. The method of claim 12, wherein each of the plurality of fusion apertures extends through at least two anti-migration features.

14. The method of claim 1, wherein the plurality of fusion apertures is configured to allow a plurality of boney bridges to form across the fusion implant, and wherein the at least one of the plurality of fusion apertures extends into the main body through at least one of the plurality of anti-migration features and is configured to receive one of the plurality of boney bridges therethrough, securing the fusion implant.

15. The method of claim 1, wherein the fusion implant further includes a tapered nose disposed at a distal end of the fusion implant, the tapered nose is configured to assist in insertion of the fusion implant.

16. The method of claim 15, wherein the tapered nose is configured so a surface of the tapered nose forms an angle between about 30 and about 70 degrees relative to a longitudinal axis of the fusion implant.

* * * * *